United States Patent [19]
Farbood et al.

[11] Patent Number: 5,420,022
[45] Date of Patent: May 30, 1995

[54] FERMENTATION PROCESS FOR PREPARING PHENYLACETIC ACID USING PHENYLALANINE AS A STARTING MATERIAL

[75] Inventors: Mohamad I. Farbood, Holmdel; Robert W. Blocker, Lakewood; Lynda B. McLean, Matawan; Lewis G. Scharpf, Fair Haven, all of N.J.

[73] Assignee: International Flavors & Fragrances Inc., New York, N.Y.

[21] Appl. No.: 214,298

[22] Filed: Mar. 17, 1994

[51] Int. Cl.$^6$ ............................ C12P 7/40; C12P 41/00
[52] U.S. Cl. ...................................... 435/136; 435/280; 435/822; 435/874; 435/875
[58] Field of Search ............... 435/136, 280, 822, 874, 435/875

[56] References Cited

PUBLICATIONS

Derwent Abs. of Japan 59-232095 Matsumoto et al. (Dec. 26, 1984) Abs Published May 8, 1985.
Bourgeau, et al, Can. J. Microbiol. 1983, 29(9)(abstracted at Chem. Abstracts vol. 100, 1984:3279s).
Kohmoto, et al, J. Fac. Agr., Tottori University, 1973, 8, 21–31 (abstracted at Chem. Abstracts vol. 81, 1974, 3432q).
Yusasa, et al, Agric, Biol. Chem. 1976, 40(9), 1679–85 (abstracted at Chem. Abstracts vol. 85, 1976, 174055s).
Dagley, et al, J. Gen. Microbiol. 8, 1–7 (1953) (abstracted at Chem. Abstracts 1953, 4953c).
Wantanabe, et al, Nippon Nogei Kagaku Kaishi, 1977, 51(2), 95–100 (abstracted at Chem. Abstracts vol. 86:185637e, 1977).
Uyemura, J. Agr. Chem. Soc. Japan, 17, 311–14(1941) (abstracted at Chem. Abstracts vol. 41, 1947, 4828i).

*Primary Examiner*—Herbert J. Lilling
*Attorney, Agent, or Firm*—Arthur L. Liberman

[57] ABSTRACT

Described is a process for preparing phenylacetic acid using phenylalanine as a starting material by means of first culturing one or more organisms from the genus Pseudomonas or from the genus Comamanas or mutants thereof; then intimately contacting the organism culture with racemic phenylalanine or L-phenylalanine or a mixture thereof in the presence of a gaseous oxygen-containing composition such as air and in aqueous media; and finally recovering phenylacetic acid from the fermentation broth.

7 Claims, 13 Drawing Sheets

FIG. I

GLC PROFILE FOR EXAMPLE II

GLC PROFILE FOR EXAMPLE II

GC MASS SPECTRUM FOR EXAMPLE III

GLC PROFILE FOR EXAMPLE II

GLC PROFILE FOR EXAMPLE V

GLC PROFILE FOR EXAMPLE VI

GC MASS SPECTRUM FOR EXAMPLE VI

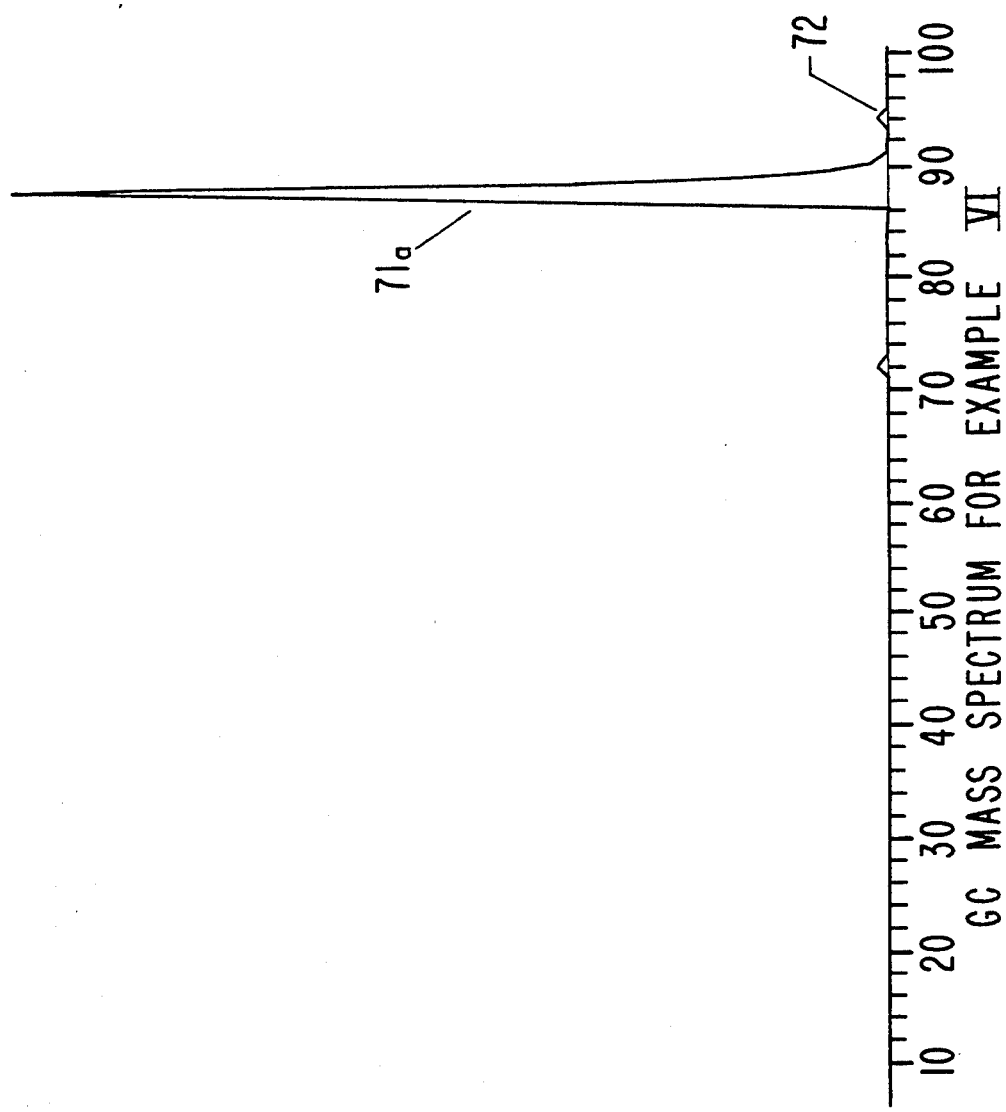
FIG. 7-A

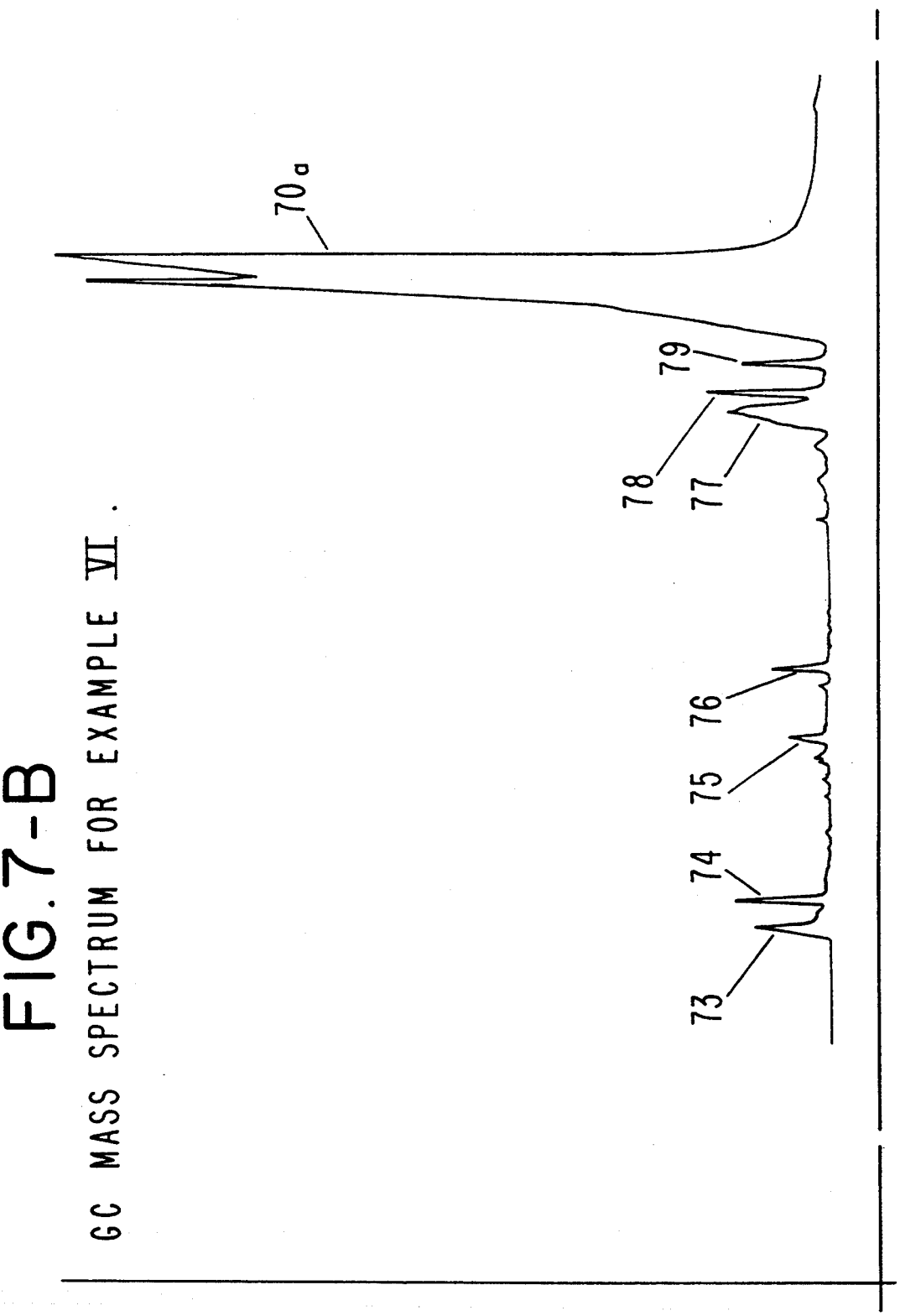
FIG.7-B GC MASS SPECTRUM FOR EXAMPLE VI.

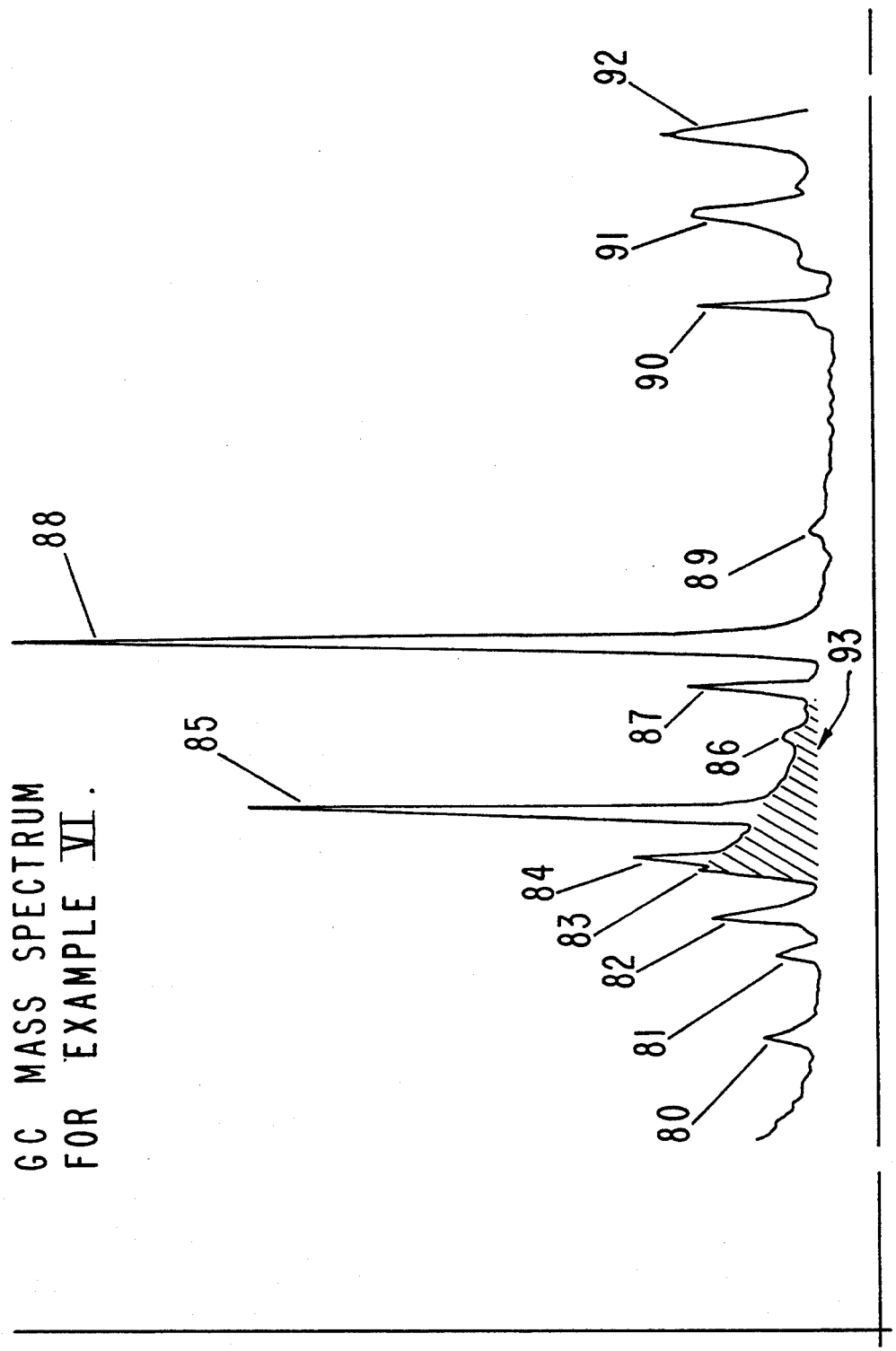

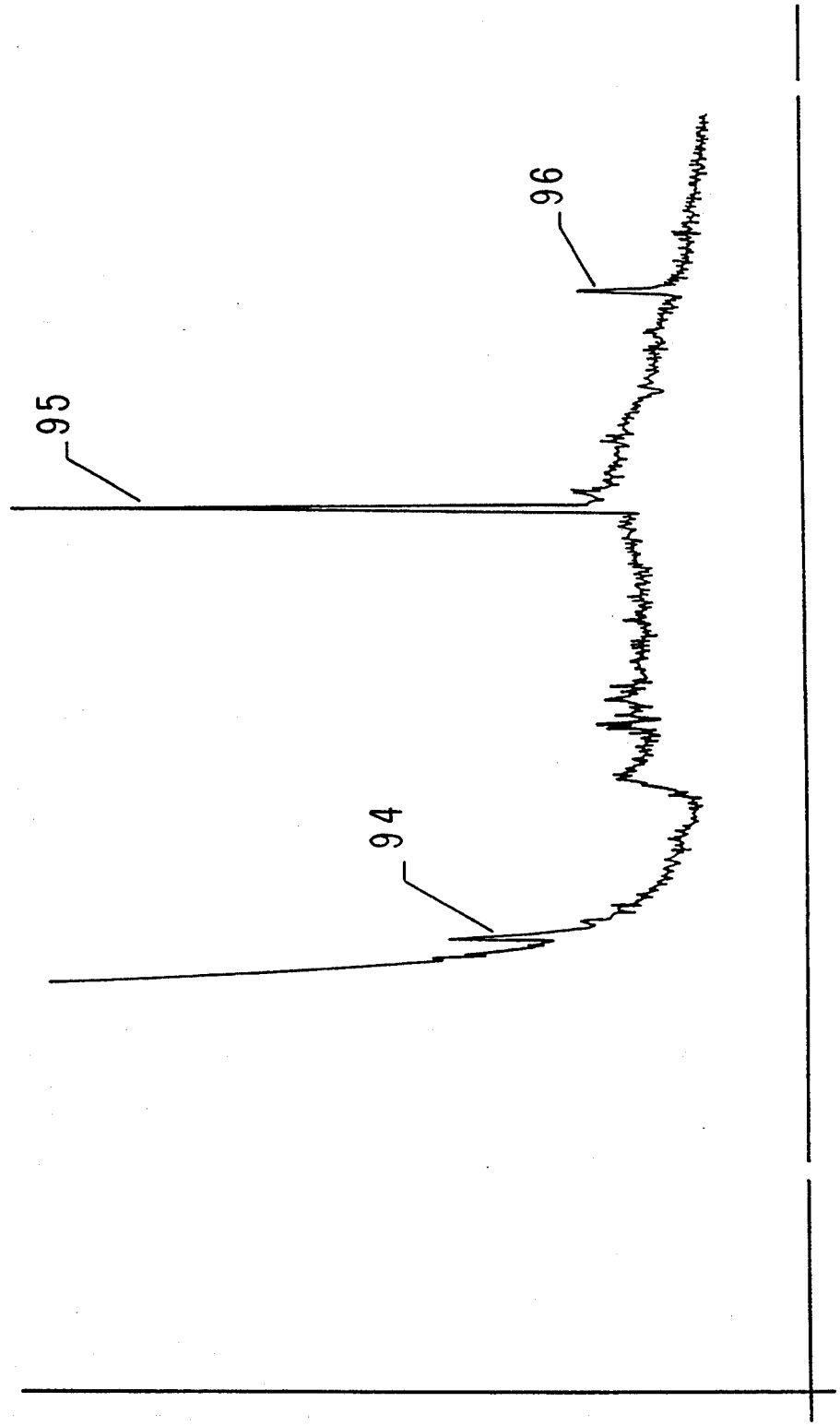

GLC PROFILE FOR EXAMPLE VI

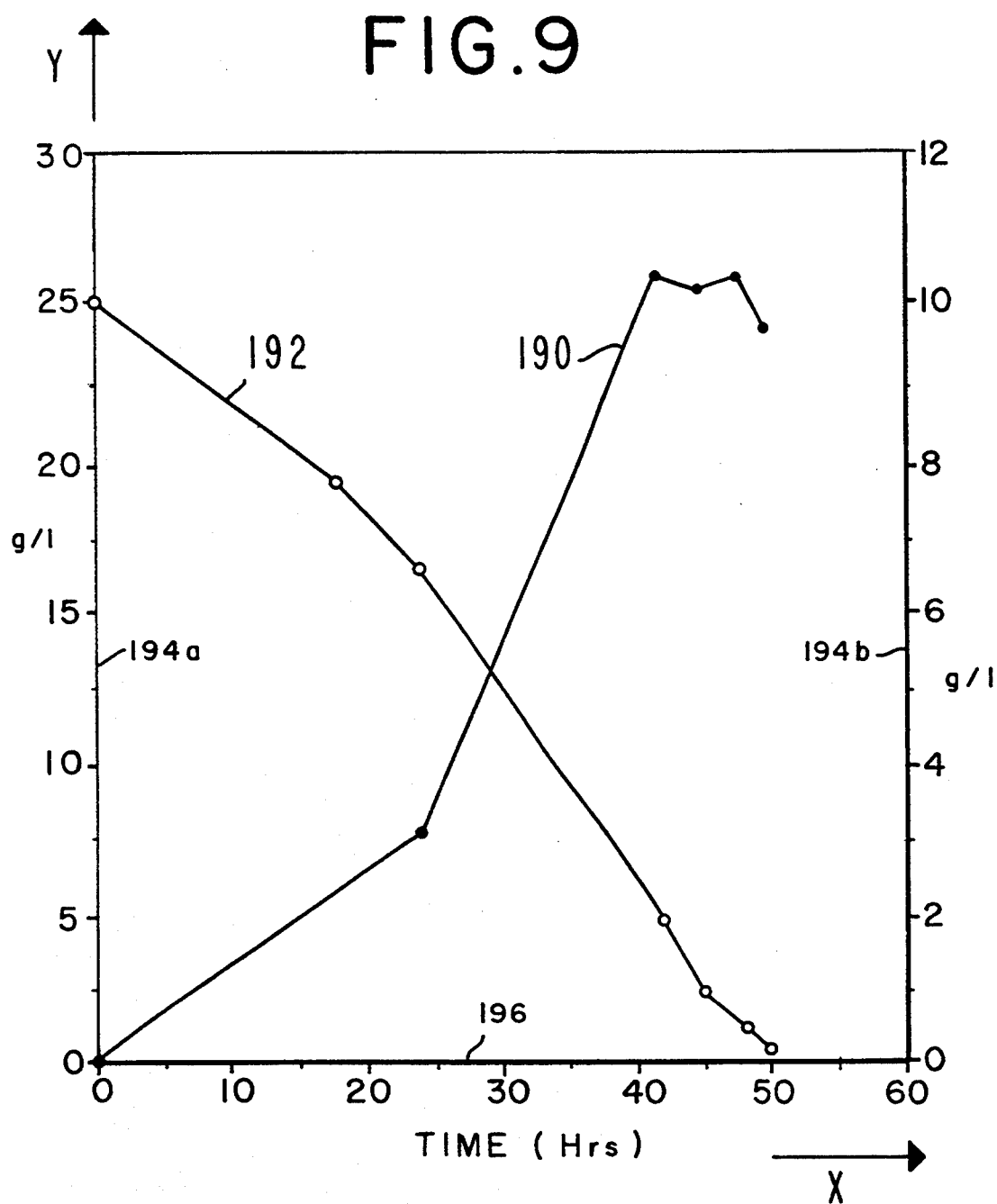

FERMENTATION PROCESS FOR PREPARING PHENYLACETIC ACID USING PHENYLALANINE AS A STARTING MATERIAL

BACKGROUND OF THE INVENTION

Our invention relates to a fermentation process for preparing phenylacetic acid using phenylalanine as a starting material with the fermentation being carried out in aqueous media and in the presence of a gaseous oxygen-containing composition such as air using an organism of the Pseudomonas genus or of the Comamanas genus or a mutant thereof. The organisms express enzymes which enable one or both of the reactions:

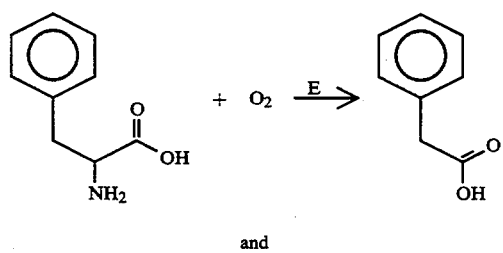

and

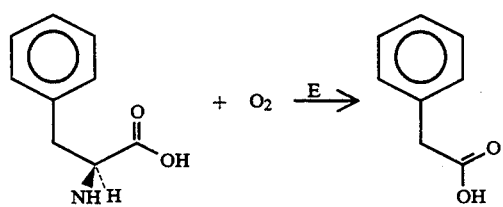

to proceed to produce phenylacetic acid having the structure:

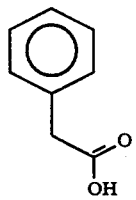

in high yield.

Phenylacetic acid has been shown to be produced from phenylalanine using fermentation type reactions but the various organisms used to carry out such reactions have not produced the phenylacetic acid in commercially available yields. A need exists for producing such phenylacetic acid in commercially useful yield in view of the usefulness of such phenylacetic acid for its organoleptic properties and as an intermediate to prepare other compounds. Thus, for example, the following references indicate production of low yields of phenylacetic acid using phenylalanine as a starting material:

(i) Bourgeau, et al; CAN. J. Microbiol. 1983, 29 (9) 1184–9 (shows the use of *Bacteroides gingivalis*);
(ii) Kohmoto, et al; J. Fac. Agr., Tottori University, 1973, 8, 21–31 (uses *Rhizoctonia solani*);
(iii) Yuasa, et al; Agric. Biol. Chem., 1976, 40 (9) 1679–85 (uses *Saccharomyces rouxii*);
(iv) Dagley, et al; J. Gen. Microbiol, 8, 1–7 (1953) (uses Vibrio O1).

Nothing in the prior art discloses the use of members of the Comamanas or Pseudomonas genus or for that matter any other organism for carrying out the reaction:

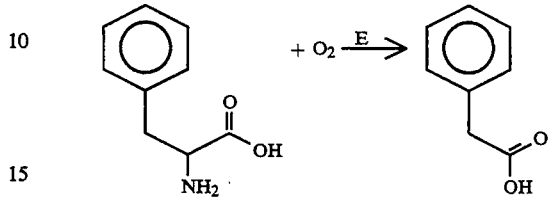

or the reaction:

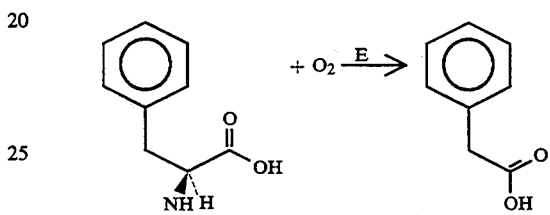

or the combination of reactions:

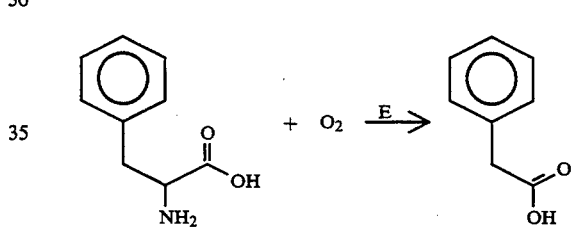

and

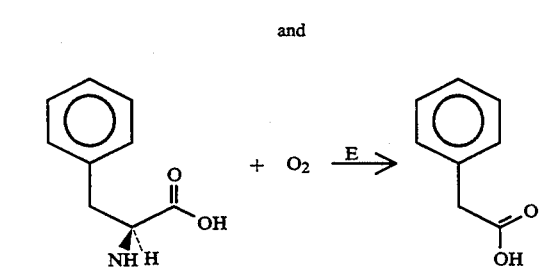

to effect production of phenylacetic acid having the structure:

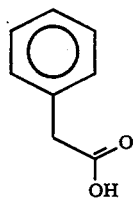

in high yield by means of fermentation.

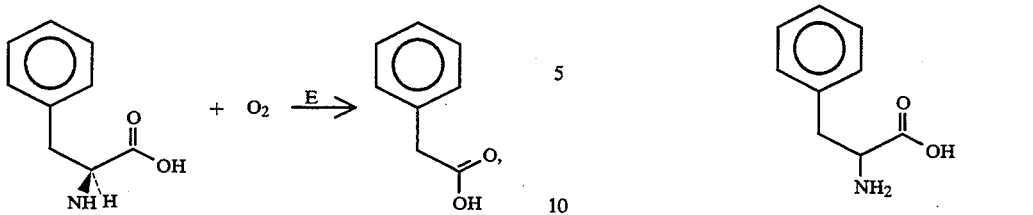

*Comamanas testosteroni*, ATCC 17409 (48 hours reaction).

Figure 1:
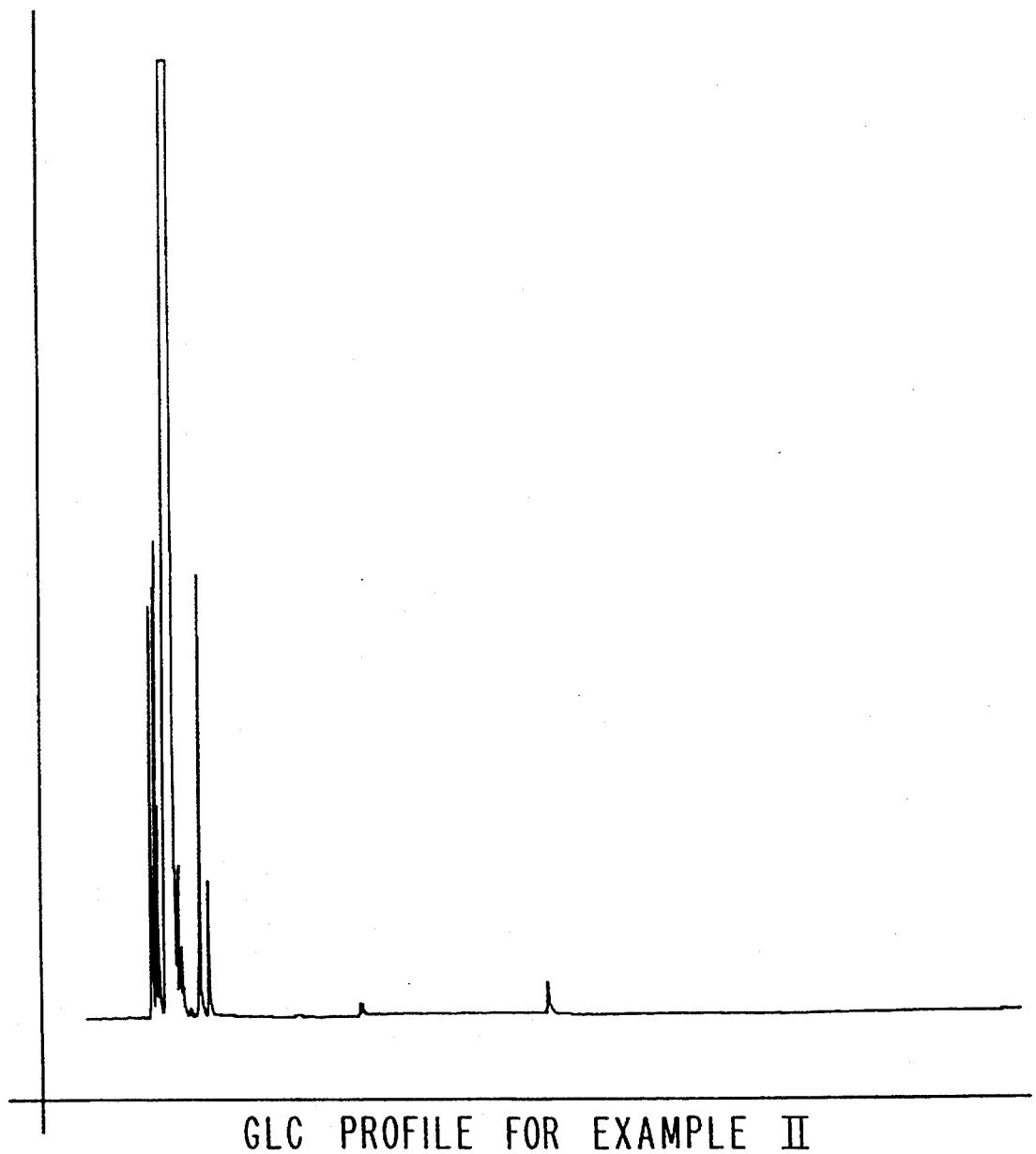
FIG. 1 is the GLC profile for a reaction product of Example II using as the organism to effect the reaction.
Figure 2:
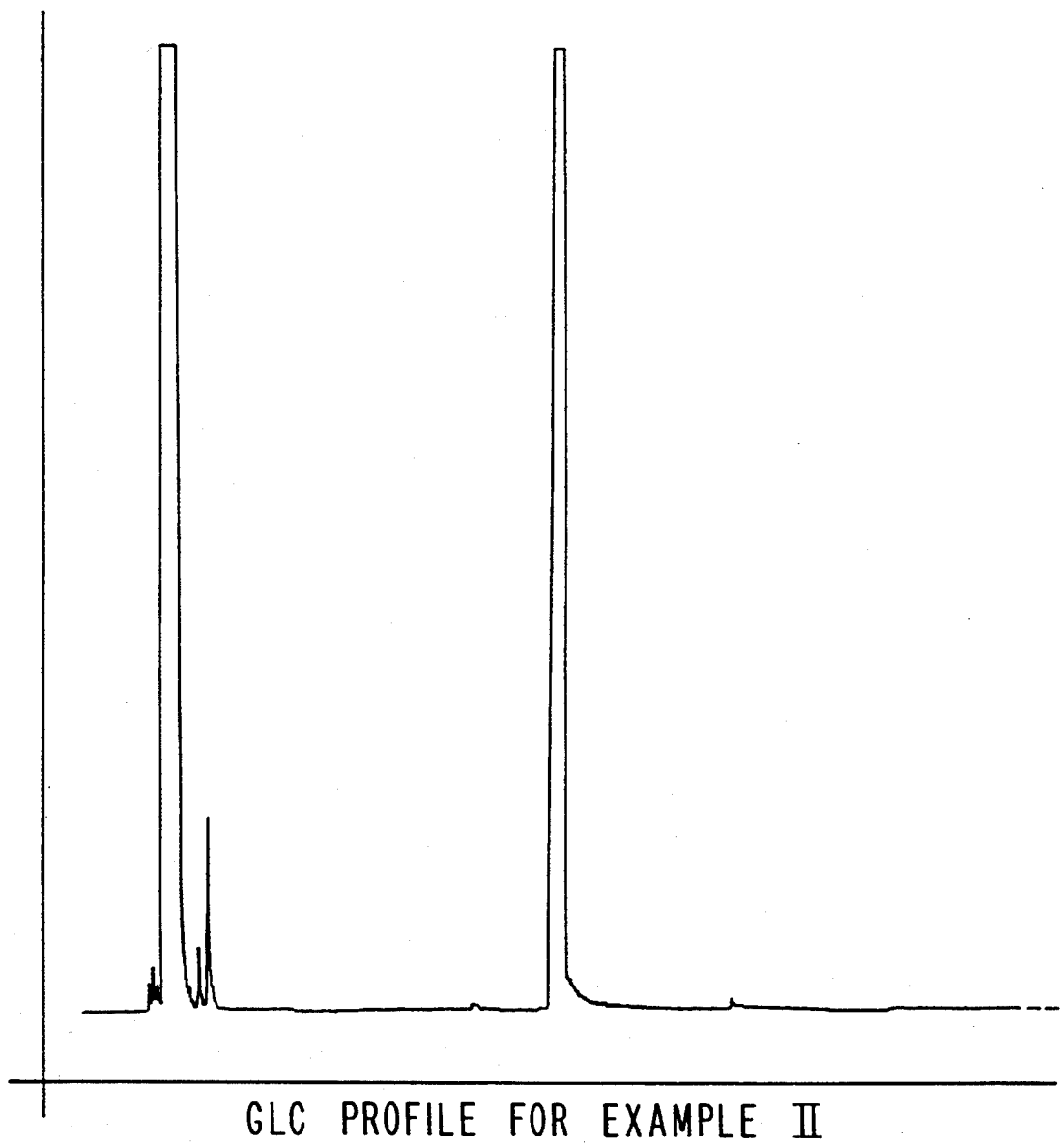

FIG. 2 is the GLC profile for a reaction product of Example II wherein in effecting the reaction:

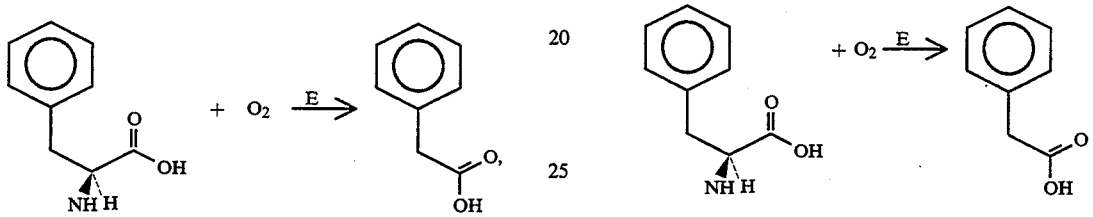

the organism used is *Pseudomonas gladioli* var *gladioli*, ATCC 10247.

Figure 3:
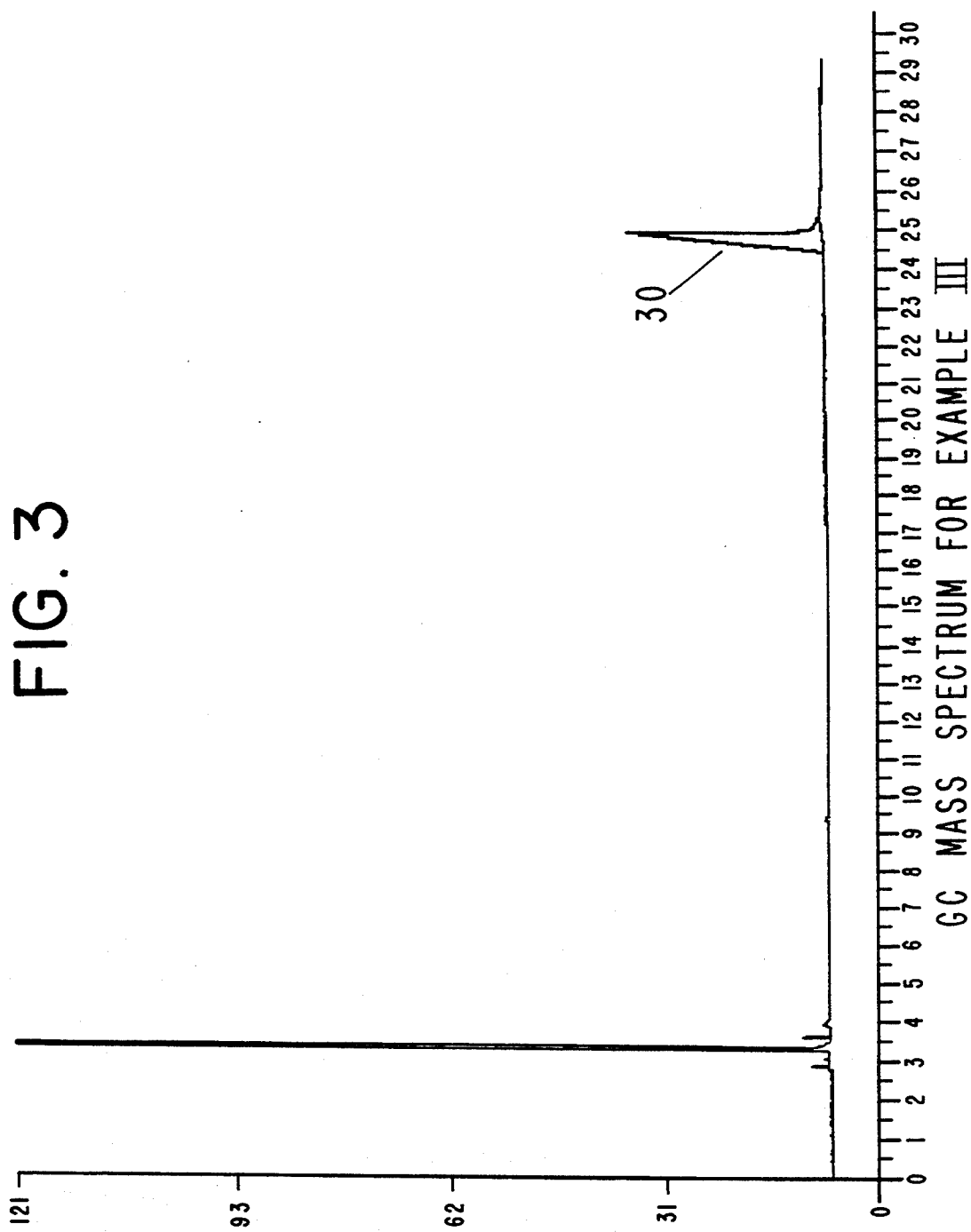

FIG. 3 is the GC mass spectrum for the reaction product of Example III wherein the example uses as the organism *Pseudomonas cepacia*, ATCC 25416.

Figure 4:
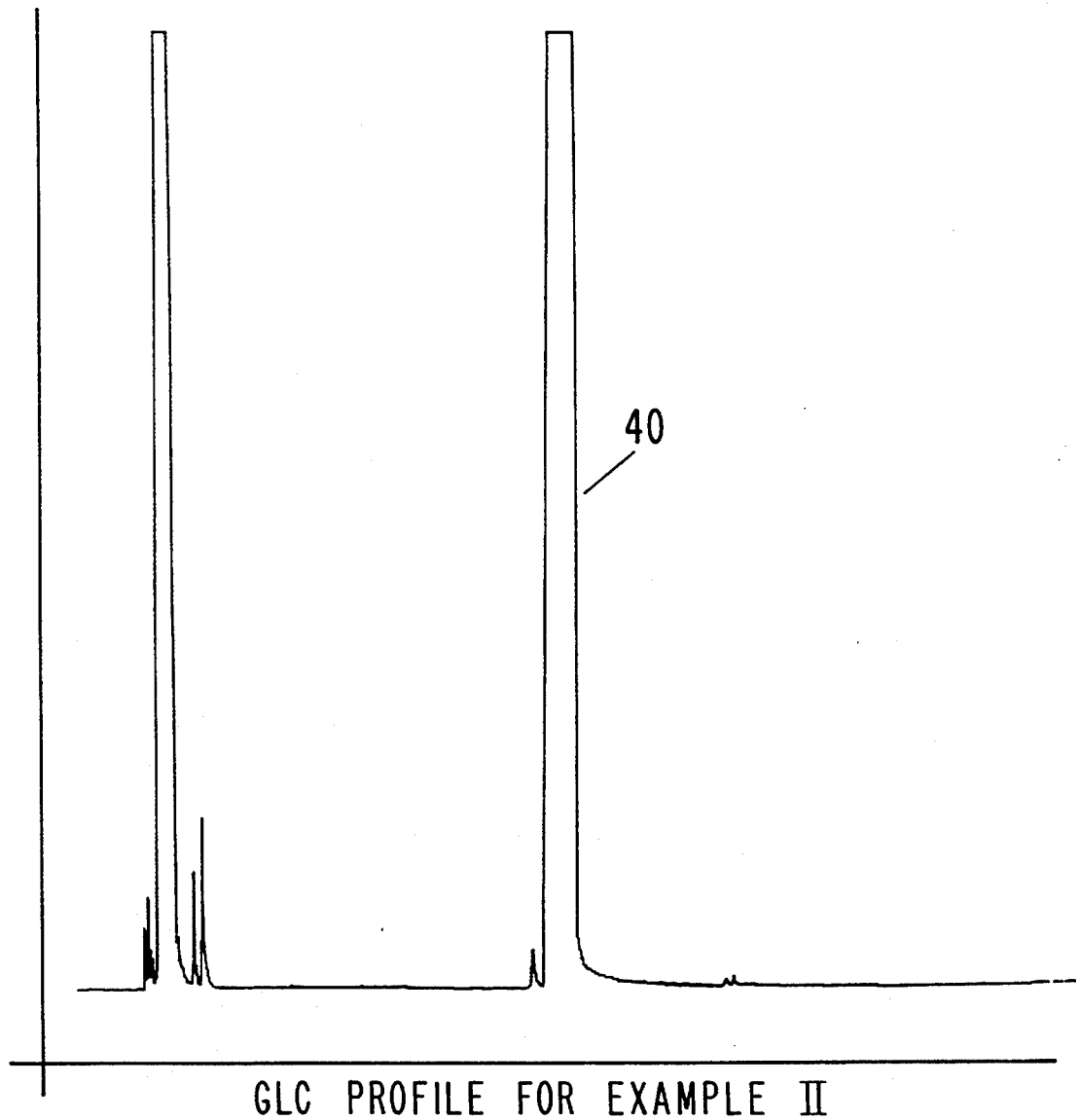

FIG. 4 is the GLC profile for the reaction product of Example IV containing phenylacetic acid having the structure:

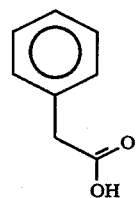

produced using the organism *Pseudomonas gladioli* var *gladioli*, ATCC 10247 (incubation period: 48 hours).

Figure 5:
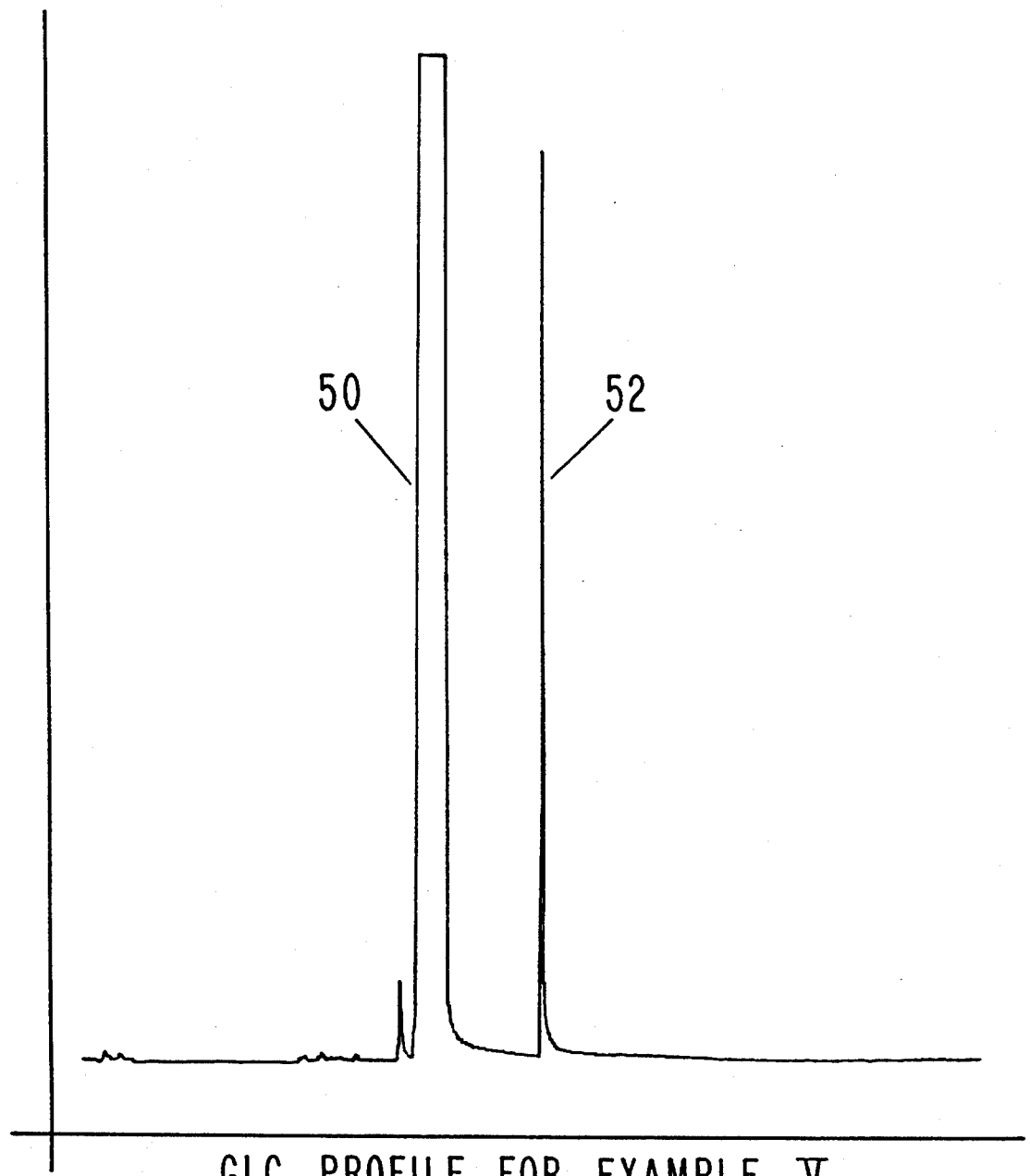

FIG. 5 is the GLC profile for the reaction product of Example V containing phenylacetic acid having the structure:

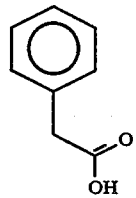

and phenylacetamide having the structure:

using as the organism to effect the reaction *Pseudomonas gladioli* var *gladioli*, ATCC 10247.

Figure 6:
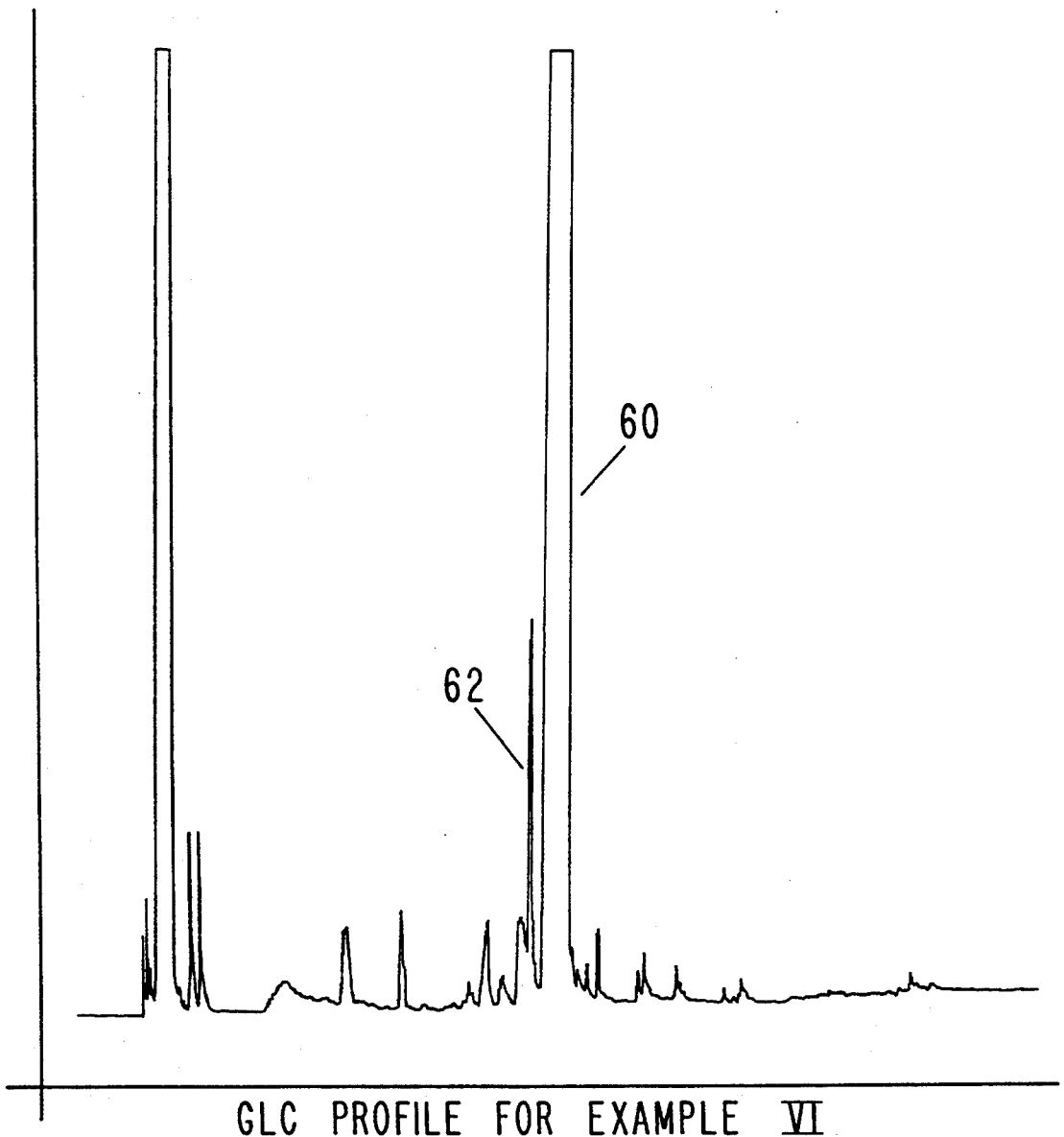

FIG. 6 is the GLC profile for the reaction product of Example VI following a special extraction procedure as set forth in detail in Example VI, supra, wherein the reaction:

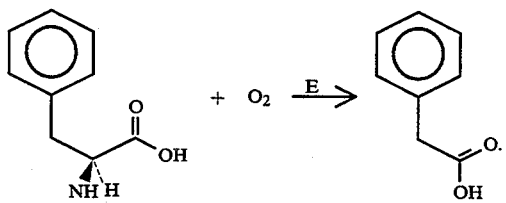

is effected using the organism *Pseudomonas gladioli* var *gladioli*, ATCC 10247 (Conditions: 60M×0.53 mm methyl silica (fused silica) column programmed from 100°–235° C. at 5° C. per minute).

Figure 7:
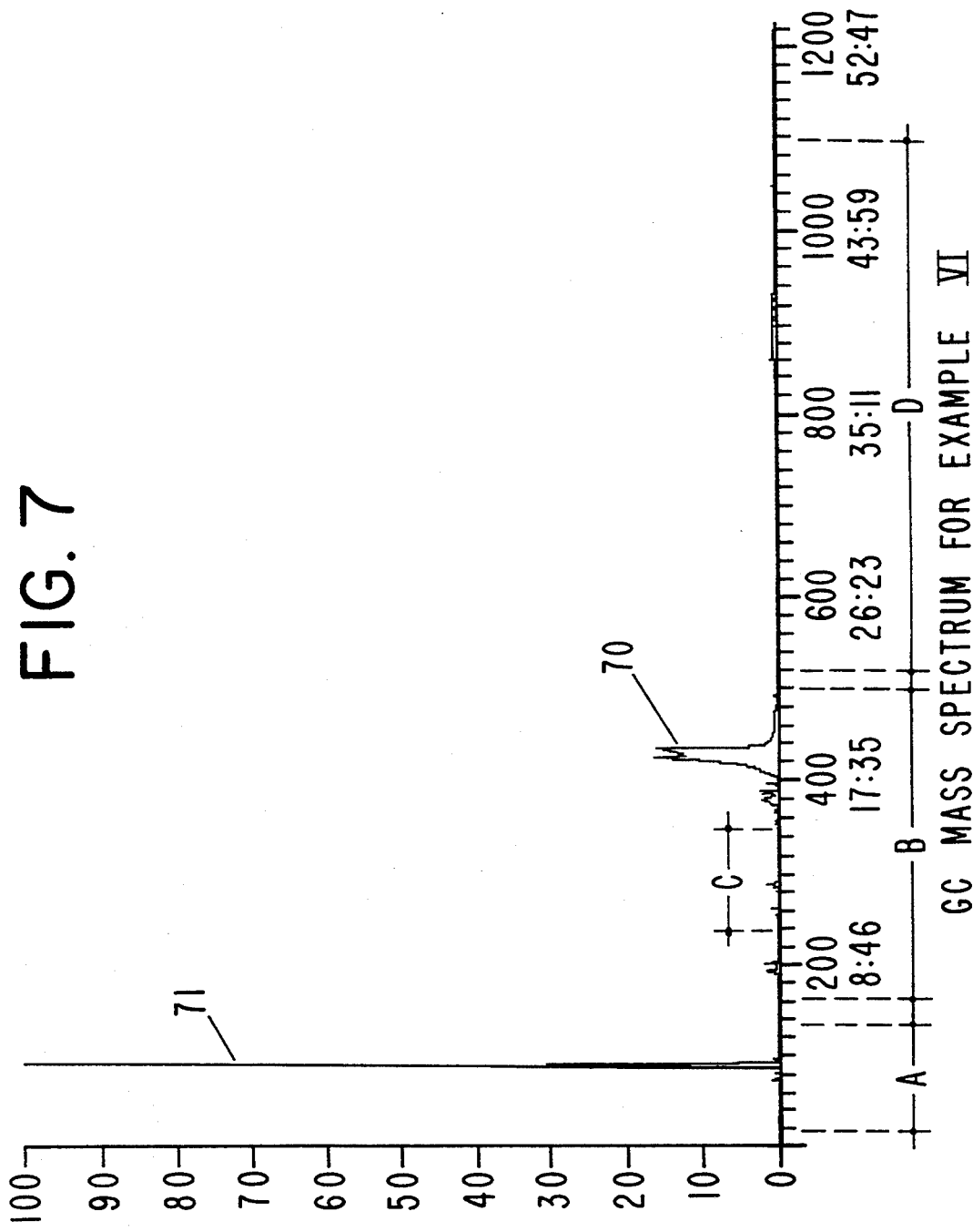

FIG. 7 is the GC mass spectrum for the reaction product of Example VI.

FIG. 7A is an enlargement of the section indicated using the letter "A" of the GC mass spectrum of FIG. 7.

FIG. 7B is an enlargement of that portion of the GC mass spectrum of FIG. 7 indicated by the letter "B".

FIG. 7C is an enlargement of that portion of the GC mass spectrum of FIG. 7 indicated by the letter "C".

FIG. 7D is an enlargement of that portion of the GC mass spectrum of FIG. 7 indicated by the letter "D".

Figure 8:
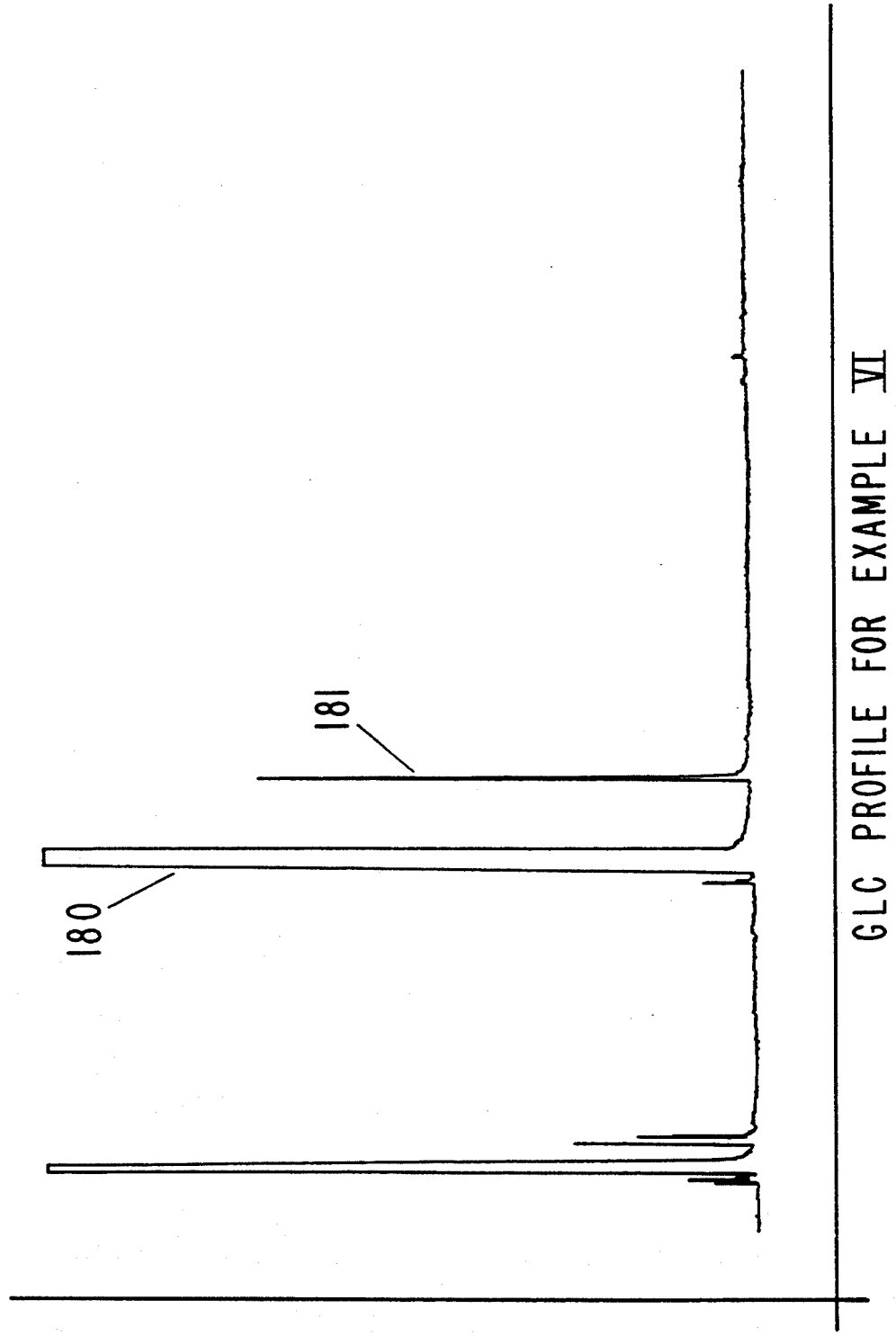

FIG. 8 is another GLC profile of the distilled phenylacetic acid produced according to Example VI.

FIG. 9 is a graph showing the increase of reaction product phenylacetic acid versus the decrease of reactant phenylalanine over a period of time from 0–50 hours during the reaction:

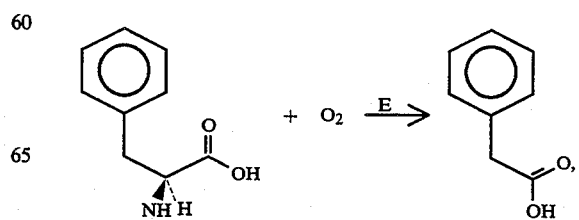

DETAILED DESCRIPTION OF THE DRAWINGS

Referring to FIG. 3, FIG. 3 is the GC mass spectrum for the reaction product of Example III. The peak indicated by reference numeral 30 is the peak for phenylacetic acid having the structure:

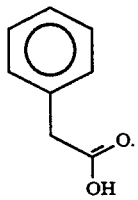

FIG. 4 is the GLC profile for the reaction product of Example IV. The peak indicated by reference numeral 40 is the peak for phenylacetic acid having the structure:

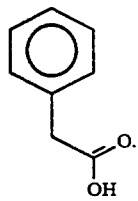

FIG. 5 is the GLC profile for the reaction product of Example V. The peak indicated by reference numeral 50 is the peak for phenylacetic acid having the structure:

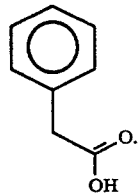

The peak indicated by reference numeral 52 is the peak for phenylacetamide having the structure:

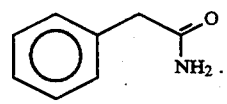

FIG. 6 is the GLC profile for an extracted distilled filtrate of the reaction product of Example VI containing the reaction product, phenylacetic acid having the structure:

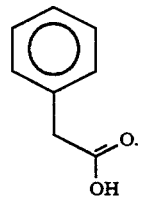

The peak indicated by reference numeral 60 is the peak for phenylacetic acid having the structure:

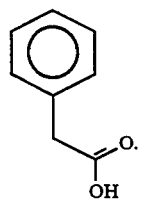

The peak indicated by reference numeral 62 is for the compound having the structure:

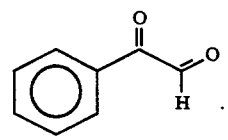

FIG. 7 is the GC mass spectrum for the reaction product of Example VI. The peak indicated by reference numeral 71 is for the compound having the structure:

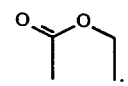

The peak indicated by reference numeral 70 is for phenylacetic acid having the structure:

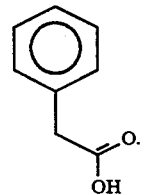

FIG. 7A is an enlargement of that portion of FIG. 7 indicated by the letter "A". The peak indicated by reference numeral 71A is for the compound having the structure:

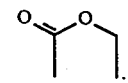

The peak indicated by reference numeral 72 is for the compound having the structure:

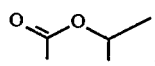

FIG. 7B is an enlargement of that portion of the GC mass spectrum of FIG. 7 indicated by the letter "B". The peak indicated by reference numeral 73 is the peak for the compound having the structure:

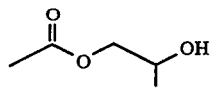

The peak indicated by reference numeral 74 is for the compound having the structure:

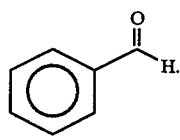

The peak indicated by reference numeral 75 is for the compound having the structure:

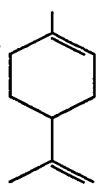

The peak indicated by reference numeral 76 is the peak for the compound having the structure:

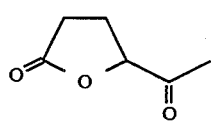

The peak indicated by reference numeral 77 is for the compound having the structure:

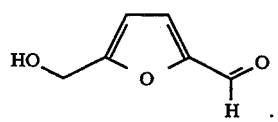

The peak indicated by reference numeral 78 is for the compound having the structure:

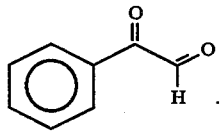

The peak indicated by reference numeral 79 is for the compound having the structure:

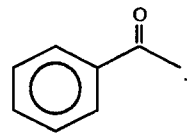

FIG. 7C is an enlargement of that portion of the GC mass spectrum of FIG. 7 indicated by the letter "C". The peak indicated by reference numeral 80 is for the compound having the structure:

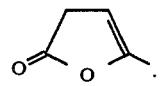

The peak indicated by reference numeral 81 is for the compound having the structure:

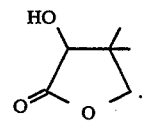

The peak indicated by reference numeral 83 is for the compound having the structure:

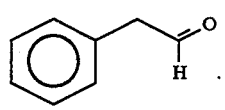

The peak indicated by reference numeral 84 is for the compound having the structure:

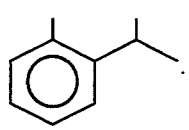

The peak indicated by reference numeral 85 is for the compound having the structure:

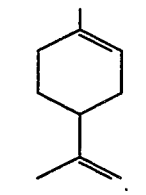

The peak indicated by reference numeral 93 is for the compound having the structure:

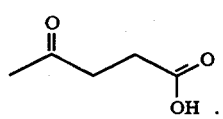

The peak indicated by reference numeral 86 is for the compound having the structure:

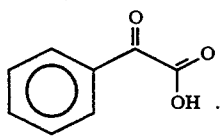

The peak indicated by reference numeral 87 is for the compound having the structure:

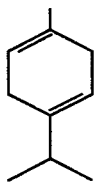

The peak indicated by reference numeral 88 is for the compound having the structure:

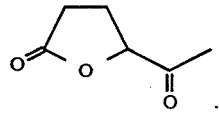

The peak indicated by reference numeral 89 is for the compound having the structure:

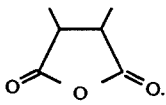

The peak indicated by reference numeral 90 is for the compound having the structure:

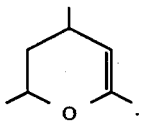

The peak indicated by reference numeral 91 is for the compound having the structure:

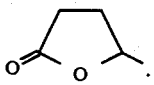

The peak indicated by reference numeral 92 is for the compound having the structure:

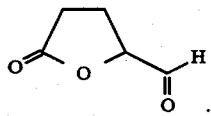

FIG. 7D is an enlargement of that portion of the GC mass spectrum of FIG. 7 indicated by the letter "D".

The peak indicated by reference numeral 94 is the peak for the compound having the structure:

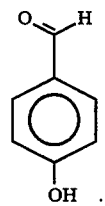

The peak indicated by reference numeral 95 is for the compound having the structure:

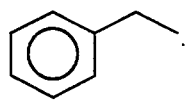

The peak indicated by reference numeral 96 is for the compound having the structure:

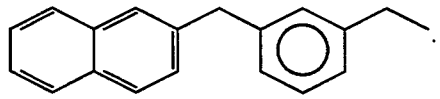

FIG. 8 is a GLC profile of distilled phenylacetic acid produced according to Example VI. The peak indicated by reference numeral 180 is the peak for phenylacetic acid having the structure:

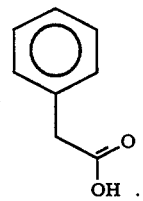

The peak indicated by reference numeral 181 is for phenylacetamide having the structure:

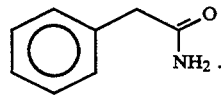

FIG. 9 is a reactant-product graph showing the rate of increase of product, phenylacetic acid and the rate of decrease of reactant, phenylalanine over a period of 50 hours during the reaction of Example VI. Reference numeral 194a is for the concentration of phenylalanine on the "y" axis. Reference numeral 194b is for the concentration of phenylacetic acid (grams per liter) on the "y" axis. The graph indicated by reference numeral 192 is for the concentration of phenylalanine with the time indicated on the "x" axis (as shown by reference numeral 196) and the concentration of the phenylalanine shown on the "y" axis indicated by reference numeral 1194a (grams per liter). The graph indicated by reference numeral 190 is the graph for time versus concentration of the product phenylacetic acid with time shown on the "x" axis, indicated by reference numeral 196 and concentration of phenylacetic acid shown on the "y" axis indicated by reference numeral 194b. The "y" axis for the phenylalanine (reference numeral 194a) extends from 0 up to 30 grams per liter. The "y" axis for phenylacetic acid, indicated by reference numeral 194b shows concentration of phenylacetic acid extending from 0 up to 12 grams per liter. The time on the "x" axis indicated by reference numeral 196 extends from 0 to 60 hours.

THE INVENTION

Our invention sets forth a process for producing phenylacetic acid having the structure:

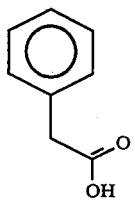

taken alone or taken together with other materials such as phenylacetamide having the structure:

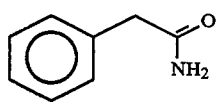

consisting essentially of the steps of:
(i) culturing one or more organisms selected from the group consisting of (a) at least one member of the genus Pseudomonas and (b) at least one member of the genus Comamanas; or mutants thereof thereby forming an organism culture;
(ii) intimately contacting said organism culture with (a) racemic phenylalanine having the structure:

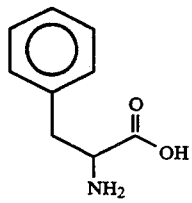

or L-phenylalanine having the structure:

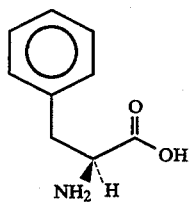

or a mixture thereof and (b) a gaseous oxygen-containing composition (such as air) in aqueous media thereby forming a phenylacetic acid-containing fermentation broth; according to the reaction:

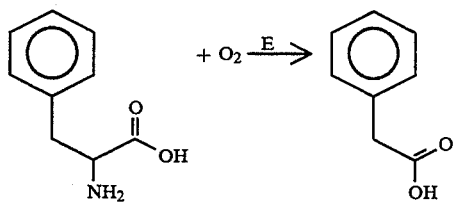

or the reaction:

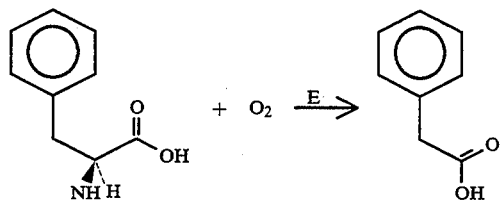

or according to both reactions:

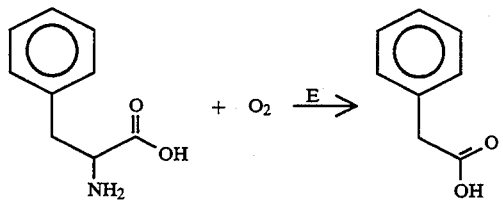

and

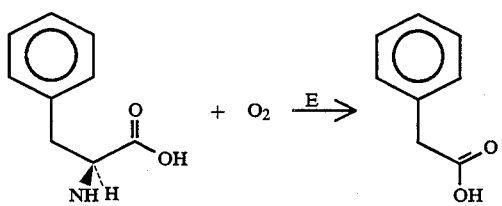

and
(iii) recovering phenylacetic acid from the fermentation broth. More specifically, the reaction:

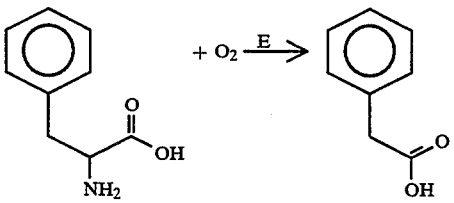

or the reaction:

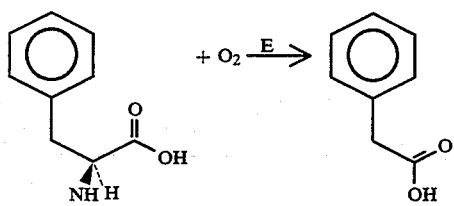

or the combination of reactions:

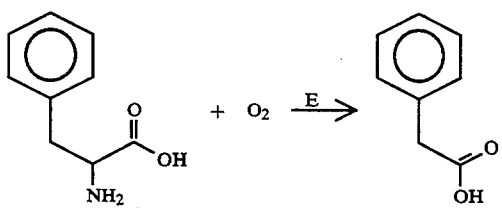

and

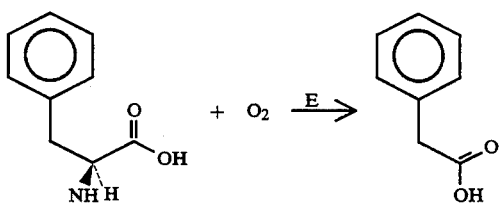

is carried out at:
(a) a pH in the range of from about 6 up to about 8, with a pH of 7 being preferred;
(b) a temperature of reaction in the range of from about 20° C. up to about 40° C. with a preferred temperature of reaction of 30° C.;
(c) a time of reaction or incubation of from about 20 hours up to about 300 hours with a preferred time of reaction or incubation of from 20 up to 50 hours:
(d) an initial phenylalanine concentration range of from about 0.8% up to about 4% in aqueous media; and
(e) aeration or oxygenation conditions of from about 0.05 v/v/m up to about 0.5 v/v/m with a preferred condition of oxygenation using air of from about 0.30 up to about 0.35 v/v/m (volume air/volume fermentation batch/minute).

Although any member of the Comamanas genus may be used in effecting one or both of the reactions:

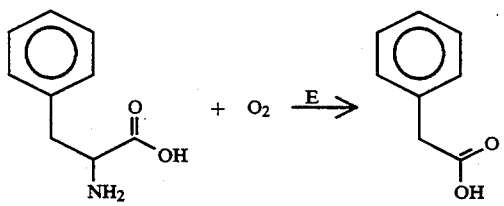

and

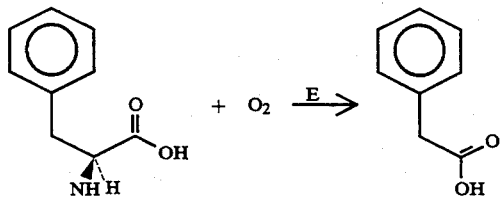

the preferred members of the Comamanas genus are:
(i) *Comamanas testosteroni*, ATCC 11996;
(ii) *Comamanas testosteroni*, ATCC 15666; and
(iii) *Comamanas testosteroni*, ATCC 17409.

Although all members of the Pseudomonas genus are useful in practicing our invention the preferred Pseudomonas species are:
*Pseudomonas cepacia*, ATCC 25416;
*Pseudomonas gladioli* var *gladioli*, ATCC 10247;
*Pseudomonas aeruginosa*, ATCC 10145;
*Pseudomonas aeruginosa*, ATCC 9721; and
*Pseudomonas aminovorans*, ATCC 23314.

Other members of the Pseudomonas genus useful in the practice of our invention are set forth in Table I of Example II, infra.

In carrying out our invention, the process is carried out using standard procedures; first forming an inoculum of the organism, for example, an inoculum of *Pseudomonas cepacia*, ATCC 25416. Thus, for example, the inoculum can be prepared by mixing beef extract, yeast extract, peptone and water; adjusting the pH to about 7; and then inoculating the resulting mixture with 0.5 ml of frozen culture of, for example, *Pseudomonas cepacia*, ATCC 25416 and aqueous dextrose. The inoculum is incubated at, for example, 150 RPM for a period of 24 hours at a temperature of, for example, 30° C.

The resulting inoculum is then admixed with a mixture of phenylalanine, salts, such as, potassium acid phosphate, magnesium sulfate, ferrous sulfate, yeast extract and mineral water. While maintaining the pH at 7, and aerating the resulting mixture and maintaining the temperature at, for example, 30° C. the mixture is agitated for a period of about 60 hours, for example.

At the end of the 60 hour period (and as stated, supra, the fermentation period can range up to 300 hours in order to enhance the yield of the phenylacetic acid) the fermentation broth is "worked up". Thus, for example, the fermentation broth is acidified to a pH of 2 and then extracted with an extraction solvent such as ethyl acetate. The resulting extract is then washed, for example, with saturated aqueous sodium chloride and the solvent evaporated under vacuum. The resulting fruit product is then distilled to yield, for example, 98.5% pure phenylacetic acid (as stated in Example III, infra).

The resulting phenylacetic acid is useful for its organoleptic properties as a "natural" flavorant or a "natural" perfume ingredient or as a intermediate to produce other products in the perfume area and in the ethical drug area.

The following examples are illustrative and our invention is limited only by the scope of the claims set forth following the examples.

All parts are by weight unless otherwise specified.

EXAMPLE I

SCREENING PROCEDURE

Medium:
A "medium" was prepared by mixing the following ingredients:

| Ingredients | Parts by Weight |
| --- | --- |
| Phenylalanine | 1.0% |
| KH$_2$PO$_4$ | 0.1% |
| MgSO$_4$.7H$_2$O | 0.05% |
| Yeast extract | 0.1% |
| Dextrose | 5.0% |

Procedure:
Organisms were inoculated into 100 ml of the above medium and incubated at 26° C., 200 RPM. The broth was monitored by TLC and UV detection.

|  | TLC Solvent: |  |
|---|---|---|
| Ethyl Acetate |  | 50% |
| Hexanes |  | 50% |
| Acetic Acid |  | 0.5% |

GROUP I

| | ATCC | TLC results | | | | |
|---|---|---|---|---|---|---|
| | | 48 hrs | 120 hrs | 144 hrs | 168 hrs | 216 hrs |
| *Pycnoporus sanguineus* | 20160 | neg | phenyl acetic acid | phenyl acetic acid | phenyl acetic acid | phenyl acetic acid |
| *Penicillium aurantiogris* | 34613 | neg | phenyl acetic acid | phenyl acetic acid | phenyl acetic acid | phenyl acetic acid |
| | | | phenyl lactic acid | phenyl lactic acid | phenyl lactic acid | phenyl lactic acid |
| *Proteus mitajiri* | 21136 | neg | phenyl acetic acid | phenyl acetic acid | phenyl acetic acid | phenyl acetic acid |
| | | | benzaldehyde | benzaldehyde | benzaldehyde | benzaldehyde |

GROUP II

| | ATCC | TLC results | |
|---|---|---|---|
| | | 72 hrs | 168 hrs |
| *Pycnoporus saguineus* | 20160 | neg | phenyl acetic acid |
| *Penicillium aurantiogris* | 34613 | neg | phenyl acetic acid |
| | | | phenyl lactic acid |
| *Proteus mitajiri* | 21136 | neg | phenyl acetic acid |
| | | | benzaldehyde |

EXAMPLE II

PHENYLACETIC ACID SCREENING PROCEDURE

INOCULUM:

The following inoculum was prepared by mixing the following ingredients, using the following parameters:

Medium:

| 0.3% | DIFCO ® Beef Extract |
|---|---|
| 0.5% | DIFCO ® Peptone |
| 0.2% | DIFCO ® Yeast Extract |
| 0.4% | Dextrose |
| 1 Liter | Deionized Water |

Parameters:
  Temperature: 30° C.
  Agitation: 150 RPM
  Duration: 24 hours
  pH=7

Five hundred ml flasks containing 50 ml of the above-prepared inoculum medium was sterilized at 121° C. for 20 minutes. Each flask was inoculated with a loopfull from a slant culture (nutrient agar) of corresponding organism. Each flask was incubated in a shaker (150 RPM) at 30° C. for 24 hours.

CULTURE SCREENING:

The following medium was prepared by mixing the following ingredients:

Medium:

| 2% | Dextrose |
|---|---|
| 0.1% | KH$_2$PO$_4$ |
| 0.05% | MgSO$_4$.7H$_2$O |
| 0.2% | DIFCO ® Yeast Extract |
| 0.5 mg | FeSO$_4$.7H$_2$O |
| 2.0 g | L-Phenylalanine |
| 100 ml | Deionized Water, |

Parameters:
  Temperature: 30° C.
  Agistation: 150 RPM
  Duration: 24–72 hours
  pH=7.

Five hundred ml flasks containing 100 ml of screening medium was sterilized at 121° C. for 20 minutes. Each flask was inoculated using 0.5% of 24 hour grown culture of each organism (as set forth in Table I, infra). Each flask was incubated in a shaker (150 RPM) at 30° C. for 24–72 hours.

Fermentation was terminated by adjusting the pH to 2 using 75% H$_2$SO$_4$. Broth was extracted two times with an equal volume of ethyl acetate. The solvent was evaporated under vacuum. The weight of crude extract was determined and analyzed by GC analysis. The results of these screening experiments are summarized in Table I as follows:

TABLE I

SCREENING OF CULTURES FOR PRODUCTION OF PHENYLACETIC ACID

| Microorganism | Culture Collection | Incubation (hrs.) | Crude Extract (g/L) | Phenylacetic Acid in Crude (%) | Phenylacetic Acid (g/L) |
|---|---|---|---|---|---|
| *Comamanas testosteroni* | ATCC 11996 | 24 | 3.5 | 44.5 | 1.5 |
| *Comamanas testosteroni* | ATCC 15666 | 48 | 1.9 | 36.9 | 0.7 |
| *Comamanas testosteroni* | ATCC 17409 | 48 | 3.9 | 12.6 | 0.5 |
| *Comamanas testosteroni* | ATCC 33083 | 24 | 6.4 | 32.1 | 2.1 |
| *Peudomonas aeruginosa* | ATCC 10145 | 72 | 3.9 | 81.5 | 3.1 |
| *Peudomonas aeruginosa* | ATCC 9721 | 72 | 2.5 | 95.0 | 2.3 |
| *Peudomonas aminovorans* | ATCC 23314 | 24 | 4.2 | 62.7 | 2.6 |
| *Peudomonas cepacia* | ATCC 25416 | 24 | 3.8 | 8.3 | 0.5 |
| *Peudomonas cruciviae* | ATCC 21283 | 72 | 7.5 | 96.6 | 7.2 |
| *Peudomonas diminuta* | ATCC 4335 | 48 | 8.8 | 41.5 | 3.7 |

TABLE I-continued

SCREENING OF CULTURES FOR PRODUCTION OF PHENYLACETIC ACID

| Microorganism | Culture Collection | Incubation (hrs.) | Crude Extract (g/L) | Phenylacetic Acid in Crude (%) | Phenylacetic Acid (g/L) |
|---|---|---|---|---|---|
| *Peudomonas fluorescens* | ATCC 12842 | 48 | 8.8 | 8.6 | 0.8 |
| *Peudomonas fluorescens* | ATCC 12983 | 72 | 5.5 | 82.3 | 4.5 |
| *Peudomonas fluorescens* | ATCC 17513 | 48 | 3.7 | 43.4 | 1.6 |
| *Peudomonas gladioli* | ATCC 10247 | 24 | 4.3 | 97.1 | 4.1 |
| *Peudomonas gladioli* | ATCC 10248 | 72 | 3.2 | 94.8 | 3.1 |
| *Peudomonas putida* | ATCC 17453 | 24 | 5.3 | 47.1 | 2.5 |
| Peudomonas sp | ATCC 23819 | 48 | 2.0 | 51.1 | 1.0 |
| Peudomonas sp | NRRL B-2994 | 48 | 1.5 | 26.2 | 0.4 |

EXAMPLE III

PHENYLACETIC ACID PRODUCTION

INOCULUM:
Medium:
The following medium was prepared:

| 3 g | DIFCO ® Beef Extract |
|---|---|
| 5 g | DIFCO ® Peptone |
| 2 g | DIFCO ® Yeast Extract |
| 1 L | Deionized Water |

Parameters:
Temperature: 30° C.
Agitation: 150 RPM
Duration: 24 hours
The pH of the resulting mixture is maintained at 7.0, adjusted before sterilization with 50% aqueous sodium hydroxide.

Five hundred ml flasks containing 50 ml of inoculum medium was sterilized at 121° C. for 20 minutes. The flask was inoculated with 0.5 ml of frozen culture of *Pseudomonas cepacia*, ATCC 25416 and 0.4 ml of sterile 50% dextrose was added. Each flask was incubated in a shaker (150 RPM) at 30° C. for 24 hours.

PHENYLACETIC ACID PRODUCTION:
Reaction:

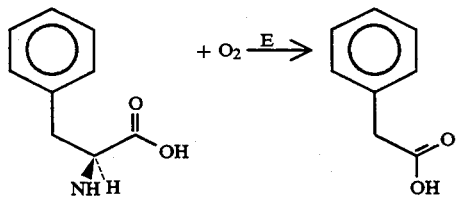

wherein E is an enzyme expressed by *Pseudomonas cepacia*, ATCC 25416.

Medium:
The following medium was prepared:

| 100 g | L-Phenylalanine |
|---|---|
| 10 g | KH$_2$PO |
| 5 g | MgSO$_4$.7H$_2$O |
| 20 g | DIFCO ® Yeast Extract |
| 50 mg | FeSO$_4$.7H$_2$O |
| 10 L | Deionized Water, |

Parameters:
Temperature: 30° C.
Aeration: 0.3 v/v/m (volume air/volume fermentation batch/minute )
Agitation: 600 RPM
Duration: 64 hours.

A pH of 7.0 was maintained during fermentation with 25% aqueous NaOH. Antifoam was added as needed: MAZU ® DF 100.

10 Liters of medium were sterilized in 14 liter fermenters at 121° C. for 20 minutes. After sterilization, 400 grams of sterile 50% dextrose and 50 ml of 24 hours grown inoculum were added. During the fermentation the sugar was monitored and maintained at 0.5% using 50% sterile solution of dextrose.

A sample of broth was acidified to pH 2 using 75% H$_2$SO$_4$. The broth was extracted three times with an equal volume of ethyl acetate. The combined extracts were washed twice with saturated NaCl. The solvent was evaporated under vacuum. The crude product was distilled using a microdistillation oven and analyzed by GC analysis. 3.5 Grams per liter of distilled product having 98.5% purity was obtained (having the structure:

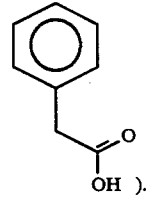

).

EXAMPLE IV

PHENYLACETIC ACID PRODUCTION

INOCULUM:
Medium:
The following medium was prepared:

| 5 g | DELTOWN ® SE50MK Soy Peptone |
|---|---|
| 2 g | DIFCO ® Yeast Extract |
| 10 g | KH$_2$PO$_4$ |
| 5 g | MgSO$_4$.7H$_2$O |
| 1 L | Deionized Water, |

A pH of 7.0 was maintained and adjusted before sterilization with 50% aqueous sodium hydroxide solution.
Parameters:
Temperature: 30° C.
Agitation: 150 RPM
Duration: 24 hours.

A 500 ml flask containing 50 ml of inoculum medium was sterilized at 121° C. for 20 minutes. The flask was inoculated with 0.5 ml of frozen culture of *Pseudomonas gladioli* var *gladioli*, ATCC 10247 and 0.4 ml of sterile 50% dextrose was added. The flask was incubated in a shaker (150 RPM) at 30° C. for 24 hours.

PHENYLACETIC ACID PRODUCTION:
Reaction:

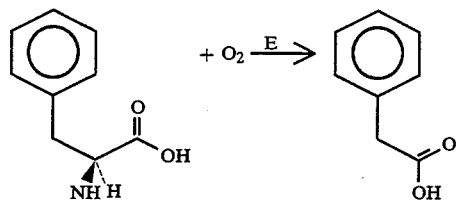

Medium:
The following medium was prepared:

| | |
|---|---|
| 250 g | L-Phenylalanine |
| 10 g | KH$_2$PO$_4$ |
| 5 g | MgSO$_4$.7H$_2$O |
| 20 g | TASTONE ® 900 (a Bakers yeast extract, spray-dried trademark of Red Star Specialty Products of 433 East Michigan Street, Milwaukee, Wisconsin 53201, a division of Universal Foods Corporation) |
| 50 mg | FeSO$_4$.7H$_2$O |
| 10 L | Deionized Water, |

A pH of 7 was maintained during fermentation with 25% aqueous sodium hydroxide solution. Antifoam: Mazu ® DF 100, was automatically added as needed.

10 Liters of medium were sterilized in 14 liter fermenters at 121° C. for 20 minutes. After sterilization, 600 grams of sterile 50% aqueous dextrose and 50 ml of 24 hours-grown inoculum were added. During the fermentation the sugar was monitored and maintained at 0.5% using 50% sterile solution of dextrose.

A sample of broth (100 ml) was acidified to a pH of 2 using 85% H$_3$PO$_4$. The broth was extracted three times with an equal volume of ethyl acetate. The combined extracts were washed twice with saturated aqueous sodium chloride. The solvent was evaporated under vacuum. The crude product was distilled using a microdistillation oven and analyzed by GC analysis. 10.5 Grams per liter of distilled product (phenylacetic acid having the structure:

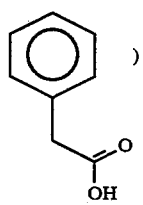

having 99.3% purity was obtained.

EXAMPLE V
PHENYLACETIC ACID PRODUCTION

A procedure the same as set forth in Example III was carried out with the exception that the phenylalanine concentration used was 3%. The phenylacetic acid production was run using an 800 liter volume rather than a 10 liter volume. 9. 5 Grams per liter of distilled product (phenylacetic acid having the structure:

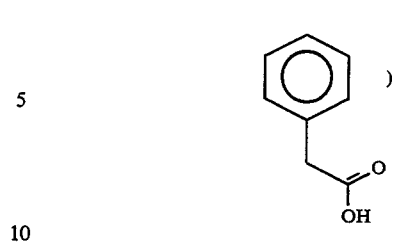

having 97.6% purity was obtained after 53 hours of fermentation.

EXAMPLE VI
PHENYLACETIC ACID PRODUCTION
PART A—LABORATORY BATCH:
Inoculum:
Medium:
The following medium was prepared:

| | |
|---|---|
| 5.0 g | DELTOWN ® SE50MK Soy Peptone |
| 2 g | TASTONE ® 900 (a Bakers yeast extract, spray-dried trademark of Red Star Specialty Products of 433 East Michigan Street, Milwaukee, Wisconsin 53201, a division of Universal Foods Corporation) |
| 1.0 g | KH$_2$PO$_4$ |
| 0.5 g | MgSO$_4$.7H$_2$O |
| 1 L | Deionized Water |

The pH was adjusted to 7.0 before sterilization, using 50% aqueous sodium hydroxide.
Parameters:
Temperature: 30° C.
Agitation: 150 RPM
Duration: 24 hours A 500 ml flask containing 50 ml of inoculum medium was sterilized at 121° C. for 20 minutes. The flask was inoculated with 0.5 ml of a frozen culture of *Pseudomonas gladioli* var *gladioli*, ATCC 10247 and 0.4 ml of sterile 50% aqueous dextrose was added. The flask was incubated in a shaker (150 RPM) at 30° C. for 24 hours.
PHENYLACETIC ACID PRODUCTION:
Medium:
A medium was prepared by mixing the following ingredients:

| Amount | Ingredient |
|---|---|
| 250 g | L-Phenylalanine |
| 10 g | KHPO$_4$ |
| 5 g | MgSO$_4$.7H$_2$O |
| 20 g | TASTONE ® 900 (a Bakers yeast extract, spray-dried trademark of Red Star Specialty Products of 433 East Michigan Street, Milwaukee, Wisconsin 53201, a division of Universal Foods Corporation) |
| 50 mg | FeSO$_4$.7H$_2$O |
| 10 L | Deionized Water |

Parameters:
Temperature: 30° C.
Aeration: 0.35 v/v/m (volume air/volume fermentation batch/minute )
Agitation: 600 RPM
Duration: 48 hours A pH of 7.0 was maintained during fermentation using 25% aqueous sodium hydroxide. Antifoam, MAZU ® DF 100 was automatically added as needed.

10 Liters of medium were sterilized in a 14 liter fermenter at 121° C. for 20 minutes. After sterilization, 600 grams of sterile 50% aqueous dextrose and 50 ml of 24 hour-grown inoculum prepared, supra, were added. During the fermentation the sugar was periodically monitored and cerelose powder was added as needed to prevent depletion of the sugar.

A sample of broth (100 ml) was acidifed to a pH of 2 using 85% H3PO4. The broth was extracted three times with an equal volume of ethyl acetate. The combined extracts were washed twice with saturated aqueous sodium chloride. The solvent was evaporated under vacuum. The crude product was distilled using a microdistillation oven and analyzed by GC analysis. 10 Grams per liter of distilled product (phenylacetic acid having the structure:

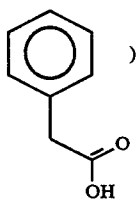

having 99.3% purity was obtained.
PART B—PILOT PLANT BATCH
Inoculum
Medium:

A medium was prepared by mixing the following ingredients in the following amounts:

| Amount | Ingredient |
|---|---|
| 25.0 g | DELTOWN ® SE50MK Soy Peptone |
| 10.0 g | TASTONE ® 900 (a Bakers yeast extract, spray-dried trademark of Red Star Specialty Products of 433 East Michigan Street, Milwaukee, Wisconsin 53201, a division of Universal Foods Corporation) |
| 5.0 g | KH2PO4 |
| 2.5 g | MgSO4.7H2O |
| 1.0 g | Antifoam |
| 5 L | Deionized Water. |

The pH was adjusted to 7.0 using 50% aqueous sodium hydroxide before sterilization.
Parameters:
Temperature: 30° C.
Aeration: 0.4 v/v/m ( volume air/volume fermentation batch/minute)
Agitation: 600 RPM
Duration: 18 hours.

A fermenter containing 5 liters of fermentation broth was sterilized at 121° C. for 20 minutes. The fermenter was inoculated with 2 ml of a frozen culture of *Pseudomonas gladioli* var *gladioli*, ATCC 10247 and 40 grams of sterile aqueous dextrose were added. The inoculum was ready for further use in 18 hours. The inoculum had a final pH of about 8.0.
PHENYLACETIC ACID PRODUCTION:
Reaction:

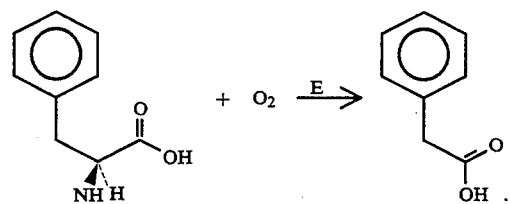

Medium:
A medium was prepared by admixing the following ingredients the amounts stated:

| Amount | Ingredient |
|---|---|
| 24.0 kg | L-Phenylalanine |
| 1.6 kg | TASTONE ® 900 (a Bakers yeast extract, spray-dried trademark of Red star Specialty Products of 433 East Michigan Street, Milwaukee, Wisconsin 53201, a division of Universal Foods Corporation) |
| 800.0 g | KH2PO4 |
| 40.0 g | MgSO4.7H2O |
| 4.0 g | FeSO4.7H2O |
| 8.0 g | Antifoam |
| 750 liters | Deionized Water. |

Parameters:
Temperature: 30° C.
Aeration: 0.35 v/v/m (volume air/volume fermentation batch/minute )
Agitation: 150 RPM
Duration: 48 hours.

A pH of 7.0 was maintained during fermentation using 50% aqueous sodium hydroxide. Antifoam: MAZU ® BF 100 was automatically added as needed.

750 Liters of medium were sterilized in a 300 gallon fermenter at 121° C. for 30 minutes. After sterilization 50 liters of sterile 50% dextrose and 5 liters of 18 hours-grown inoculum were added. During the fermentation the sugar was periodically monitored and cerelose powder was added as needed to prevent depletion of sugar.

A sample of broth (100 ml) was acidifed to a pH of 2 using 85% H3PO4. The broth was extrated three times with an equal volume of ethyl acetate. The combined extracts were washed twice with saturated aqueous sodium chloride. The solvent was evaporated under vacuum. The crude product was distilled using a microdistillation over and analyzed by means of GLC analysis. 9.5 Grams per liter of distilled product (phenylacetic acid having the structure:

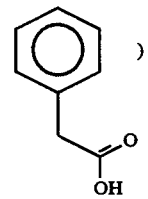

having 99.3% purity was obtained.
Product Recovery
METHOD A—Solvent Extraction:
The pH was adjusted to about 3.0 using citric acid before sterilization. After sterilization of the broth, clarification was carried out using a centrifuge. The clarified broth was extracted three times using ethyl acetate each time. The solvent was removed under vacuum at low temperature (40° C.) to prevent transesterification.
METHOD B—(Alternate Method of Purification)

After sterilization, the broth was clarified and concentrated to 30% by distilling off 70% of the total batch volume. Sodium chloride was then added to give a concentration of 20% in the concentrate. The pH was adjusted to about 3 using citric acid. The resulting product (precipitate) was recovered by vacuum filtration. The vacuum filtration uses "filter aid". The resulting "filter aid"-containing product was extracted twice with equal weights of ethyl acetate. The ethyl acetate was removed and processed according to the aforementioned procedure.

FIG. 6 is the GC mass spectrum for the resulting product.

The resulting product was then subjected to fractional distillation as follows:

| Fraction No. | Vapor Temp. (°C.) | Liquid Temp. (°C.) | Vacuum mm/Hg. Pressure |
|---|---|---|---|
| 1 | 23/40 | 23/70 | 15.0 |
| 2 | 40 | 80 | 10.0 |
| 3 | 150 | 152 | 4.0 |
| 4 | 150 | 160 | 3.0 |
| 5 | 150 | 160 | 3.0 |
| 6 | 150 | 162 | 3.0 |
| 7 | 150 | 160 | 3.0 |
| 8 | 146 | 165 | 2.5 |
| 9 | 150 | 220 | 3.0. |

Fractions 1 and 2 were substantially all solvents (ethyl acetate). Fractions 3–9 were substantially all phenylacetic

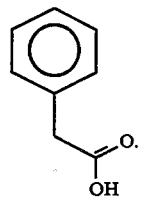

The phenylacetic acid thus formed (bulked fractions 3–9) was then crystallized from 95% aqueous ethyl alcohol. (Melting point: 75°–76° C.).

What is claimed is:

1. A process for producing phenylacetic acid having the structure:

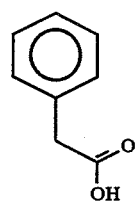

consisting essentially of the steps of:
(i) culturing one or more organisms selected from the group consisting of (a) at least one member of the genus Pseudomonas and (b) at least one member of the genus Comamanas; thereby forming an organism culture;

(ii) intimately contacting said organism culture with
(a) racemic phenylalanine defined according to the structure:

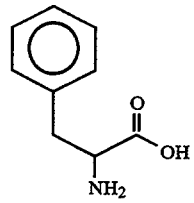

or L-phenylalanine having the structure:

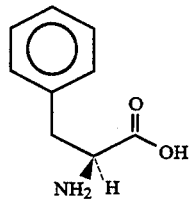

or mixtures thereof; and (b) a gaseous oxygen-containing composition in aqueous media thereby forming a phenylacetic acid fermentation broth according to the reaction:

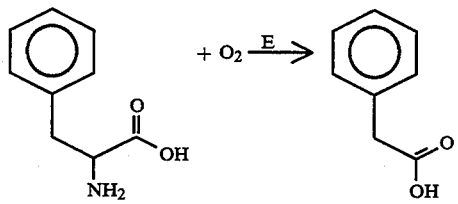

or the reaction:

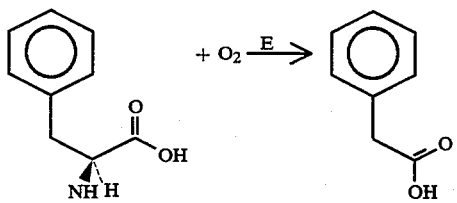

or according to both reactions:

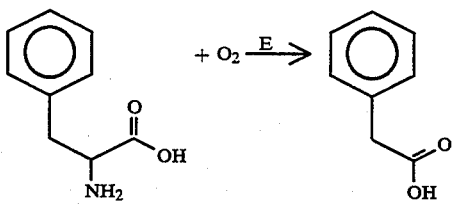

and

-continued

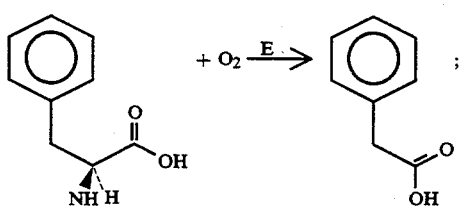

and (iii) recovering phenylacetic acid from the fermentation broth.

2. The process of claim 1 wherein the reaction:

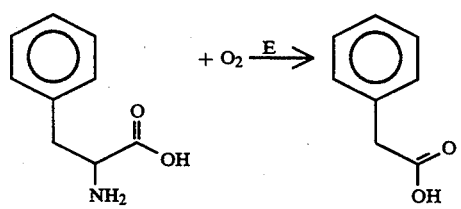

or the reaction:

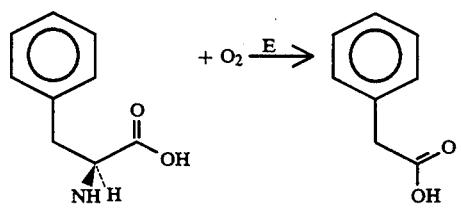

or the combination of reactions:

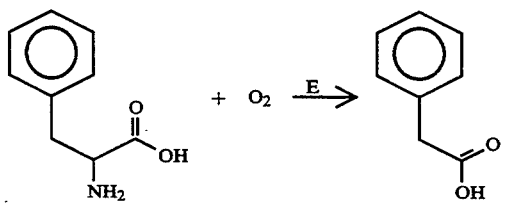

and

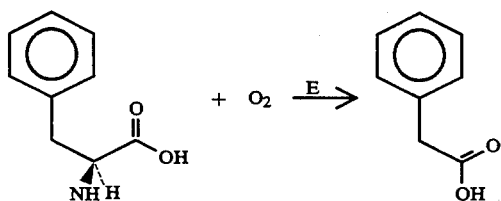

are carried out at:
(a) a pH of from about 6 up to about 8;
(b) a temperature of from about 20° C. up to about 40° C.;
(c) a time of from about 20 up to about 300 hours; and
(d) an initial phenylalanine concentration of from about 0.8 up to about 4%.

3. The process of claim 1 wherein the organism cultured is of the Pseudomonas genus.

4. The process of claim 2 wherein the organism cultured is of the Pseudomonas genus.

5. The process of claim 3 wherein the Pseudomonas organism is *Pseudomonas gladioli* var *gladioli*, ATCC 10247.

6. The process of claim 4 wherein the Pseudomonas organism is *Pseudomonas gladioli* var *gladioli*, ATCC 10247.

7. The process of claim 2 wherein the reaction:

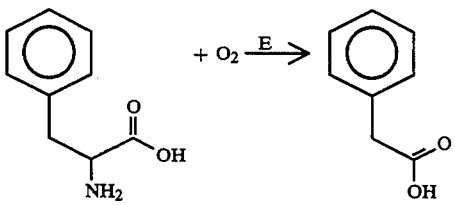

or the reaction:

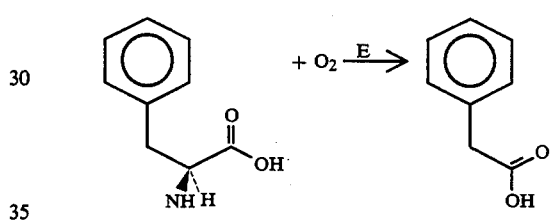

or the combination of reactions:

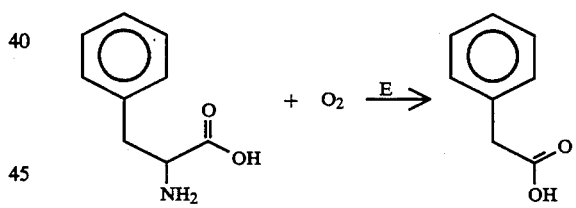

or

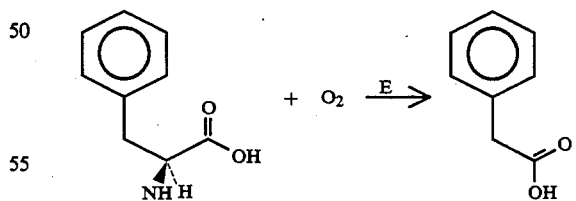

are carried out at a pH of 7; a temperature of 30° C. and a time of from about 24 hours up to about 72 hours using an initial phenylalanine concentration of from 1 up to 3% in aqueous media.

* * * * *